US008916827B2

(12) United States Patent
Frey et al.

(10) Patent No.: US 8,916,827 B2
(45) Date of Patent: Dec. 23, 2014

(54) DEVICE AND SYSTEM FOR SELECTIVELY DETECTING GAS COMPONENTS OR CONCENTRATIONS OF GAS COMPONENTS IN GAS TO BE ANALYZED AND METHOD FOR OPERATING SUCH DEVICE

(75) Inventors: Alexander Frey, Augsburg (DE); Harry Hedler, Germering (DE); Philip Clissold Howell, Riemerling (DE)

(73) Assignee: Siemens Aktiengesellschaft, Munich (DE)

( * ) Notice: Subject to any disclaimer, the term of this patent is extended or adjusted under 35 U.S.C. 154(b) by 103 days.

(21) Appl. No.: 13/817,413

(22) PCT Filed: Aug. 11, 2011

(86) PCT No.: PCT/EP2011/063805
§ 371 (c)(1),
(2), (4) Date: Feb. 15, 2013

(87) PCT Pub. No.: WO2012/022663
PCT Pub. Date: Feb. 23, 2012

(65) Prior Publication Data
US 2013/0284928 A1 Oct. 31, 2013

(30) Foreign Application Priority Data

Aug. 16, 2010 (DE) .......................... 10 2010 034 428

(51) Int. Cl.
*G01N 21/00* (2006.01)
*G01N 33/00* (2006.01)
(Continued)

(52) U.S. Cl.
CPC ............ *G01N 33/0027* (2013.01); *B82Y 20/00* (2013.01); *G01N 21/774* (2013.01); *G02B 6/1225* (2013.01); *G01J 3/108* (2013.01); *G01N 21/7746* (2013.01); *G01N 21/0303* (2013.01); *G01N 21/3504* (2013.01)
USPC ...................................... 250/338.5

(58) Field of Classification Search
CPC ....................................... B82Y 20/00

USPC ........................................................ 250/338.5
See application file for complete search history.

(56) References Cited

U.S. PATENT DOCUMENTS 7,973,924 B2 7/2011 Noda et al.
2002/0096492 A1 7/2002 George et al.
(Continued)

FOREIGN PATENT DOCUMENTS

DE 10 2005 008 077 A1 8/2006
DE 102005008077 A1 * 8/2006
(Continued)

OTHER PUBLICATIONS

Degirmenci et al: "2-D Numerical Analysis of Metallic Band-Gap Crystal Waveguide in THz"; 34th International Conference on Infrared, Millimeter, and Terahertz Waves; IEEE; Sep. 2009; pp. 1-2.

(Continued)

*Primary Examiner* — David Porta
*Assistant Examiner* — Abra Fein
(74) *Attorney, Agent, or Firm* — Staas & Halsey LLP

(57) ABSTRACT

A photonic crystal, which is a periodically arranged structure made of free-standing columns, has a base material of at least one metal or a metal alloy. Intermediate spaces between the columns allow passage of a gas to be analyzed. The photonic crystal has predefined imperfections, by which at least one resonator is formed, the resonant frequency of which is in a frequency range which is absorbed by a gas component to be detected. A heating unit heats at least some of the columns and at least one detector element extracts the energy present in the resonator in the heated state under the action of the gas to be analyzed. The device may have extremely small dimensions and very low energy consumption.

14 Claims, 6 Drawing Sheets

(51) Int. Cl.
  *B82Y 20/00* (2011.01)
  *G02B 6/122* (2006.01)
  *G01J 3/10* (2006.01)
  *G01N 21/35* (2014.01)
  *G01N 21/77* (2006.01)
  *G01N 21/03* (2006.01)

(56) References Cited

U.S. PATENT DOCUMENTS

| | | | |
|---|---|---|---|
| 2005/0017178 A1* | 1/2005 | Ogawa et al. | 250/339.07 |
| 2006/0188398 A1 | 8/2006 | Yano et al. | |
| 2006/0198567 A1* | 9/2006 | Levy et al. | 385/12 |
| 2006/0285114 A1 | 12/2006 | Cao et al. | |

FOREIGN PATENT DOCUMENTS

| | | |
|---|---|---|
| DE | 102010034428.1 | 8/2010 |
| DE | 10 2010 070 788 A1 | 11/2011 |
| JP | 2005-99007 | 4/2005 |
| JP | 2005-274329 | 10/2005 |
| WO | 2005/090947 A1 | 9/2005 |
| WO | 2008/117533 A1 | 10/2008 |
| WO | 2011/144392 A1 | 11/2011 |

OTHER PUBLICATIONS

Cruz-Cabrera et al.; "Demonstration of Thermal Emission Control", Society of Photo-Optical Instrumentation Engineers (SPIE) Conference Series; vol. 7591, Feb. 2010; 9 pp.
International Search Report for PCT/EP2011/063805 mailed Nov. 21, 2011.

* cited by examiner

DEVICE AND SYSTEM FOR SELECTIVELY DETECTING GAS COMPONENTS OR CONCENTRATIONS OF GAS COMPONENTS IN GAS TO BE ANALYZED AND METHOD FOR OPERATING SUCH DEVICE

CROSS REFERENCE TO RELATED APPLICATIONS

This application is the U.S. national stage of International Application No. PCT/EP2011/063805, filed Aug. 11, 2011 and claims the benefit thereof. The International Application claims the benefit of German Application No. 10 2010 034 428.1 filed on Aug. 16, 2010, both applications are incorporated by reference herein in their entirety.

BACKGROUND

Described below is a device for selectively detecting gas components or a concentration of a gas component in a gas to be analyzed, a method for operating such a device and a system for the selective detection of at least two gas components or the concentrations of at least two gas components in a gas to be analyzed.

The detection of gases in the environment, in particular within closed spaces, has acquired a high degree of importance. If the concentration of gas components, for example, carbon dioxide, carbon monoxide, methane or water vapor is known, it is possible to warn of dangers in good time and therefrom to draw conclusions regarding, for example, the ventilation of spaces. Such concepts are gaining importance for the design of buildings because they offer great potential for energy saving and for more comfortable and resource-saving accommodation and working.

For selective and targeted detection of gas components or a concentration of a gas component in a gas to be analyzed, sensor elements—hereinafter called gas sensors—are used which are able to detect the concentration of one or more gases. Of decisive importance with gas sensors of this type, apart from the size thereof, is the energy consumption thereof because such sensor elements can often be operated self-sufficiently with regard to energy, that is, the energy therefor is to be drawn from the kinetic energy, heat energy and/or radiant energy of the surroundings.

A large number of measuring principles, for example, resistive, capacitive, thermal, amperometric, gravimetric, biochemical or optical measurements are known for gas sensors. Optical gas sensors are often based on the principle of absorption measurement, that is, on the fact that the gases absorb light in the infrared region in specific frequency ranges or at specific wavelengths. This is used in that light from a source is emitted at a specific wavelength along a test path, wherein the attenuation of the light due to absorption is subsequently evaluated by a sensor, for example, photometrically or thermoelectrically. In order to minimize transverse effects, a second reference path is often used, for example, in the form of a reference cell in which the absorption of the gas components to be detected is not expected.

A disadvantage of gas sensors of this type, however, is that in order to realize suitable detection sensitivity levels, very large spatial dimensions (several cm, up to several tens of cm) are required.

An alternative form of gas detection via optical absorption is possible by the use of photonic crystals. Photonic crystals are periodically structured dielectric materials which are the optical analogue of semiconductor crystals and therefore enable the production of integrated photonic circuits. Photonic crystals can be classified according to the dimensionality thereof. A distinction is therefore made between one-dimensional (1D), two-dimensional (2D) and three-dimensional (3D) photonic crystals, depending on the number of spatial directions having a periodic refractive index. Known photonic crystals are made of structured semiconductors, glasses or polymers.

DE 10 2005 008 077 A1 discloses a device for analyzing the qualitative and/or quantitative composition of fluids by a thermal radiator operating in the infrared spectral region. The radiator has a photonic crystal and generates the radiation through local temperature changes in a partial region of the photonic crystal. For this purpose, magnetic and/or electrically conductive material is introduced into the pores of the photonic crystal or the pores are coated with magnetic and/or electrically conductive material. The local temperature change is then generated by inductive and/or resistive heating of the partial region of the photonic crystal. The photonic crystal is configured such that the radiation emitted by the radiator is passed on only for a defined narrow wavelength range. For the detection of the gas, a device for regulating and/or measuring a heating output of the radiator is provided, wherein a radiator temperature is measurable at a fixed heating output or the radiator is adjusted to a constant radiation temperature and the heating power required therefor can be determined.

Silicon serves therein as the base material for the photonic crystal. However, this material has a very poor reflection factor, which significantly restricts the quality of the resonator. The detection results achievable therewith are not always satisfactory. Furthermore, the filling or coating of the pores with a magnetic and/or electrically conductive material represents a further operation in the manufacturing of the gas sensor, and this is associated with additional effort and cost. Filling the pores also leads thereto that the crystal structure can only enter at the end face thereof into an interaction with the gas to be analyzed, thereby severely reducing the sensitivity of the gas sensor. This disadvantage can be circumvented by the coating of the pores. However, the coating has the disadvantage that, for manufacturing technical reasons, the diameter and the spacing of the static silicon columns must not undershoot a particular minimum dimension, with the result that severe limits are placed on the miniaturization of the gas sensor.

SUMMARY

An aspect is a device for the selective detection of a gas component or a concentration of a gas component in a gas to be analyzed, which is easily and economically manufactured and leads to precise and reliable detection results with a small usage of space and energy. A second aspect is a simple and reliable operating method for the device. A further aspect is a system which also enables simple and reliable detection of at least two gas components or of concentrations of at least two gas components in a gas to be analyzed, with a small usage of space and energy.

The first aim is achieved with a device for selective detection of a gas component or a concentration of a gas component in a gas to be analyzed with a photonic crystal, which has a periodically arranged structure of free-standing columns, the base material of which is at least a metal or a metal alloy, wherein intermediate spaces between the columns allow the gas to be analyzed to pass through. The photonic crystal has pre-defined imperfections, for example, in the form of point defects, omitted individual elements, rows or surfaces, in the form of relatively small or relatively large individual elements or in the form of columns connected together as walls, by which at least one resonator is formed. The resonant frequency of the resonator is in a frequency range which is absorbed by the gas component to be detected. A heating device is provided for heating at least a portion of the columns and for extracting the energy present in the resonator in the heated state under the effect of the gas to be analyzed, at least one detector element is used.

According to the operating method for a device of this type, the device is exposed to the gas to be analyzed, at least a portion of the columns of the photonic crystal is heated, the energy contained in the resonator is extracted by the detector element and the existence of a gas component and/or the concentration thereof is detected depending on the energy extracted.

The device makes use of the principle of an open resonator which interacts with the gas components to be detected. The underlying concept is to change the resonator properties by the gas components to be detected and to measure the change. If the gas component is not present or is present only in a very small concentration, a low level of absorption takes place in the gas path of the resonator and the resonator contains a very high density of the radiant energy (undisrupted resonator). If, however, the gas to be analyzed which acts upon the open resonator contains the gas component to be detected in a relatively high concentration, the radiation absorption in the resonator leads to a reduction in the energy density (disrupted/influenced resonator). Therefore, based on measurement of the energy density of the resonator, conclusions can be drawn concerning the concentration of the gas component. In order to obtain reliable detection results, however, it is necessary for the resonator to operate highly frequency selectively and to have a high quality. This is achieved by at least one metal or a metal alloy that is used as the base material of the column structure of the photonic crystal and the intermediate spaces between the columns permit entry of the gas to be analyzed. Metals or metal alloys have the great advantage as compared, for example, with silicon of having a significantly better coefficient of reflection and therefore enabling the formation of resonators of significantly greater quality. Such photonic crystals with free-standing columns, the base material of which is a metal or a metal alloy can be produced, for example, by a method which is described in the older application DE 10 2010 020 788.8, which is included in its entirety in the present application for the purpose of the disclosure.

Since the wavelengths to be detected in the resonator lie only in the mm range, the resonator and thus also the device can be designed very small with regard to the spatial dimensions thereof (in the region of 1 mm3). The device has an extremely small energy requirement, since only a fraction of the thermal radiation generated by heating the photonic crystal can propagate in the form of light waves in the resonator.

If pores are generated which have a diameter which changes, in particular periodically, permitting the photoelectrochemical etching method according to the older application DE 10 2010 020 788.8, a column-shaped structure is eventually formed in which the individual columns have a changing column diameter. A structure of this type, given a suitable selection of materials and dimensioning of diameters and spacings, can be used as a three-dimensional photonic crystal. However, the device is equally usable with two-dimensional photonic crystals which can be realized by columns each having the same diameter.

According to embodiments described below in more detail, the columns have a ratio of length to diameter of greater than 100, have a minimum column diameter of 0.3 µm and/or have a column diameter which changes periodically in a ratio of greater than 1:3, which means that the columns have a maximum diameter which is more than three times the minimum diameter of the columns.

The optical properties of the photonic crystal can also be specifically influenced in that, apart from the base material, the columns are formed of at least one further material, wherein the base material and the further material have a pre-defined structure and wherein as the further material, in particular, metals and/or metal alloys and/or plastics and/or oxides, in particular thermal oxides, and/or nitrides are used.

For the detection of the radiation in the resonator or the change thereof due to external influences, various methods for introducing detector elements into the resonator are suitable. What is important herein is that the resonator is not too severely damped through the introduction of detector elements, so that the internal amplification is not destroyed. According to a very simply realized embodiment, the at least one detector element is provided by at least one unheated column of the photonic crystal because the geometric resonator structure is only insignificantly disrupted thereby.

In order to enable the most efficient possible extraction of energy in the resonator, the at least one unheated column serving as a detector element can be arranged in the edge region of the resonator.

Advantageously, the at least one detector element has at least two unheated neutral columns of the photonic crystal. The at least two unheated columns can be electrically connected to a measuring loop. If the temperature-dependence of the internal material properties of the columns in the measuring loop is exploited, then conclusions can be drawn concerning the energy transmission. Since the neutral columns of the detector element are not actively thermally heated, with the aid of the energy transmission from the resonator to the detector element, conclusions can be drawn concerning the gas concentration. A high temperature indicates a low concentration of the gas component to the detected and vice versa.

In order to determine the influence of temperature, a variety of measuring principles are conceivable in principle. Thus a resistance measurement can be used wherein the temperature dependence of the specific resistance of the closed conductor loop is utilized. The at least two columns of the detector element can be made of different materials. In that case, a thermo-voltage measurement can be carried out as an alternative. A thermoforce is measured which results from temperature differences between the open and closed ends of the measuring loop.

According to a further embodiment, the photonic crystal has further pre-defined imperfections, by which at least one reference resonator is configured, the resonant frequency of which lies within a frequency range which is not absorbed by the gas component to be detected. Thereon, a reference channel can be generated which makes the minimizing of transverse effects possible.

Many properties of photonic crystals can be scaled via simple geometric relations. Therefore, it is provided, according to an advantageous embodiment, to adjust the resonant frequency of the resonator(s) by the ratio of the diameter of the columns to the separation thereof from one another. Since the individual structural elements of the photonic crystal can be defined very precisely, for example by photolithography, this is a very suitable method for matching the resonator to the gas component to be detected.

The system for selective detection of at least two gas components or of concentrations of at least two gas components in a gas to be analyzed uses a photonic crystal. The photonic crystal, which can be two-dimensional or three-dimensional, has a periodically arranged structure of free-standing columns, the base material of which is at least one metal or a metal alloy, wherein intermediate spaces between the columns permit the passage of the gas to be analyzed. Furthermore, the photonic crystal has pre-defined imperfections by which at least two resonators are configured, the resonant frequencies of which are in a frequency range such that each is absorbed by one of the gas components to be detected. With the aid of a heating device, at least some of the columns are heated. Furthermore, at least one detector element is provided for each of the resonators, by which the energy present in the respective resonator in the heated state under the effect of the gas to be analyzed can be extracted.

The device allows a large number of resonators with different resonant frequencies to be arranged adjacent to one another in one field and, therefore, any portion of the total infrared spectrum can be covered so that any desired gas components can be detected with the system.

BRIEF DESCRIPTION OF THE DRAWINGS

These and other aspects and advantages will become more apparent and more readily appreciated from the following description of the exemplary embodiments, taken in conjunction with the accompanying drawings of which.

DETAILED DESCRIPTION OF THE PREFERRED EMBODIMENT

Figure 1:
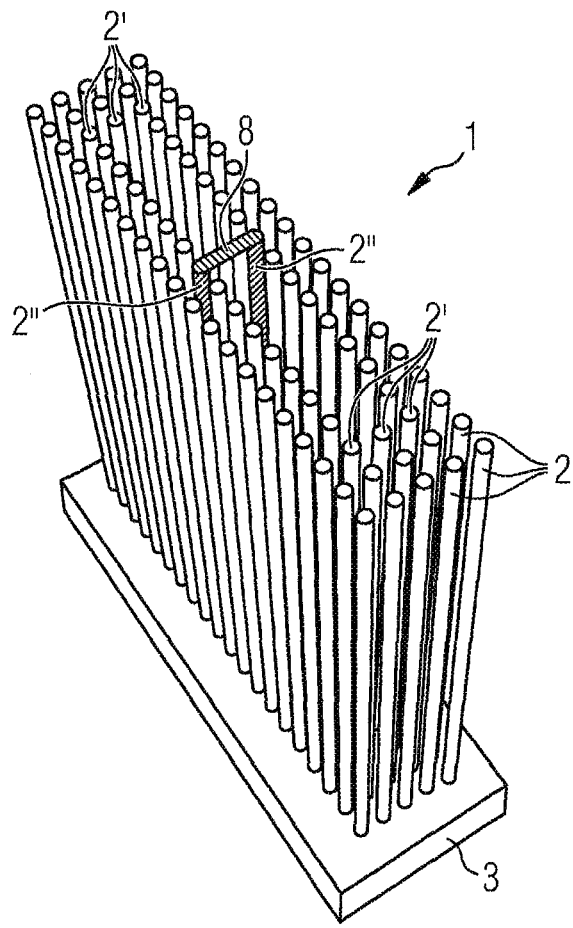
FIG. 1 is a schematic perspective representation of a device.

Reference will now be made in detail to the preferred embodiments, examples of which are illustrated in the accompanying drawings, wherein identical or functionally similar components are each identified with the same reference characters.

Figure 2:
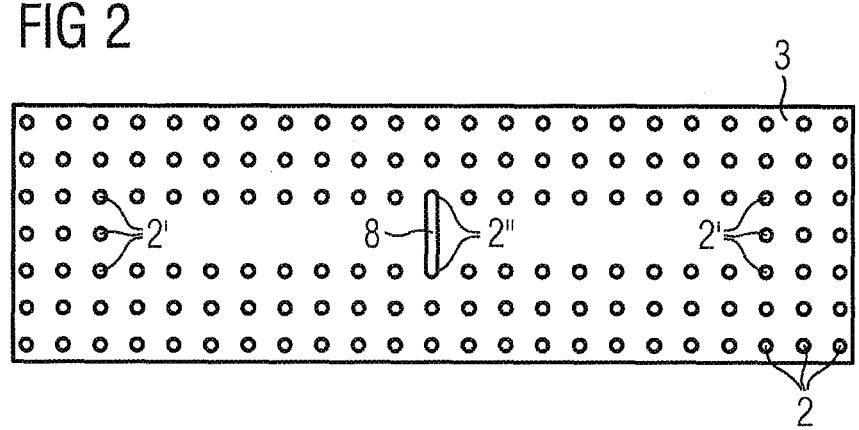
FIG. 2 is a schematic plan view of the device according to FIG. 1.
Figure 3:
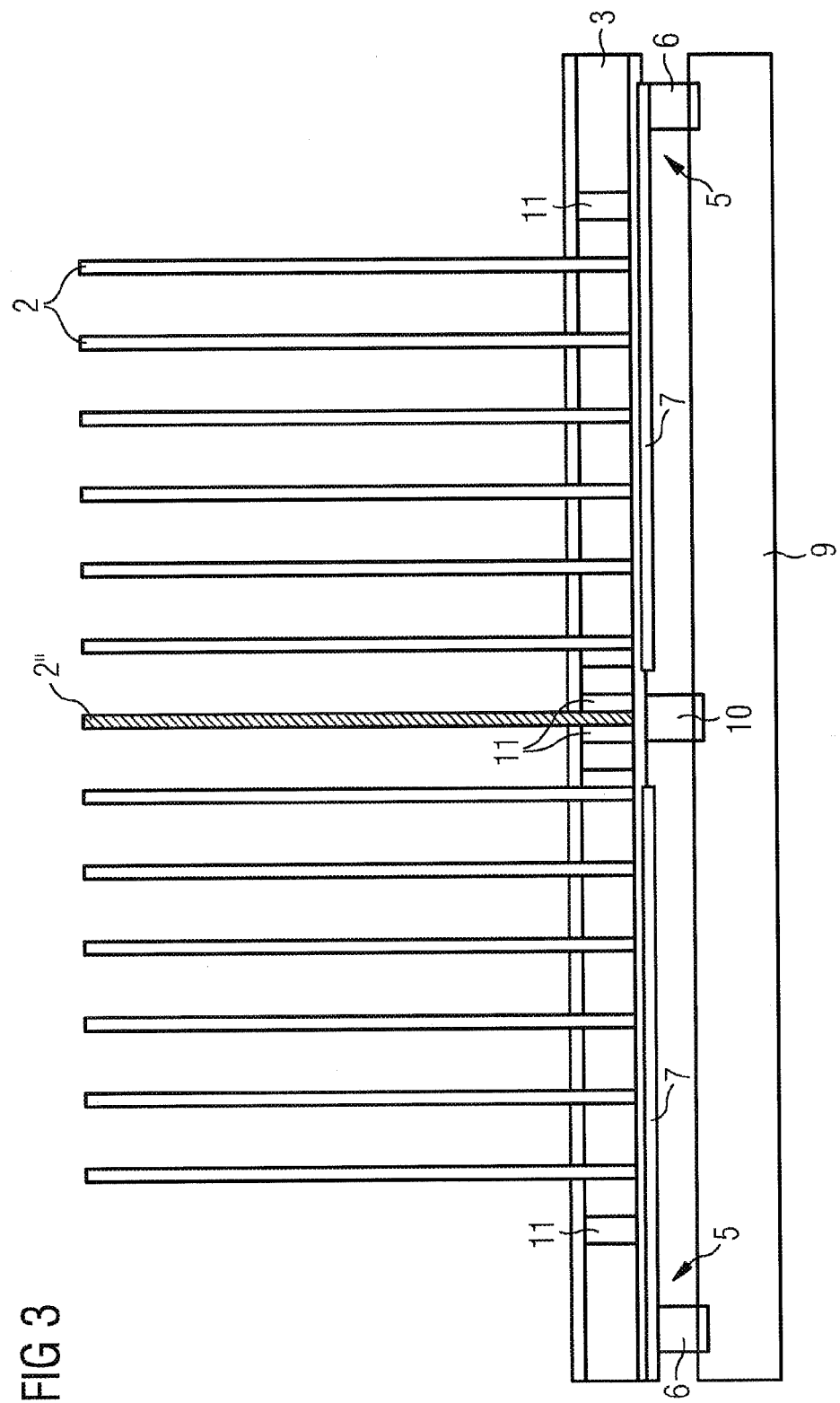
FIG. 3 is a schematic sectional representation of the device according to FIG. 1.

FIGS. 1 to 3 show schematically an embodiment of the device with a two-dimensional photonic crystal 1 which has a periodically arranged structure of free-standing columns 2 arranged on a substrate 3, for example a silicon substrate. The base material of the columns is a metal or a metal alloy. A photonic crystal 1 of this type can be made, for example, with the manufacturing method described in the older application DE 10 2010 020 788.8. In a central region, the photonic crystal 1 has predefined imperfections in the form of a missing row of columns 2. A resonator 4 is formed by the imperfections. If an energy spectrum of different frequencies is introduced into the resonator 4, then depending on the geometry of the resonator 4 and the material of the columns 2, only a few modes are stimulated to oscillate and "escalate" depending on the damping within the resonator 4. In this way, electromagnetic radiation of a wavelength (resonant frequency) according to the geometry in resonance is multiplied in the resonator 4.

The columns 2' of the photonic crystal which delimit the resonator 4 in the propagation directions of the electromagnetic radiation act as reflectors. To that extent, the material of the columns 2', in particular, influences the quality of the resonator 4 to a significant extent. Through the use of metals or metal alloys having a high reflection factor, the high quality of the resonator 4 is assured.

Apart from the base material, the columns 2 can also be made of at least one further material, the base material and the further material having a pre-defined structure and metals and/or metal alloys and/or plastics and/or oxides, in particular thermal oxides, and/or nitrides can be used as the second material. The desired optical properties of the photonic crystal 1 to be made and, in particular, of the resonator 4 ultimately determine the filling material(s) actually used and possibly the actual structure of the columns 2.

The geometry of the resonator 4 and therefore the resonant frequency are essentially determined by the diameter and spacing of the columns 2 relative to one another. Material, diameter and spacing of the columns can therefore be matched to one another such that the resonant frequency of the resonator lies within a frequency range that is absorbed by a gas component to be detected.

In order to introduce electromagnetic radiation of different wavelengths into the resonator 4, at least a portion of the columns 2 is heated with the aid of a heating device 5. This is referred to as "thermal pumping" of the photonic crystal 1. In the simplest case, the heating device 5 can include a current source (not shown in the drawings) which feeds current via electrical contacts 6 and conductor structures 7 (see FIG. 3) into the columns 2 of the photonic crystal 1 that are to be heated. In this way, resistive heating which heats the columns is brought about. Other heating devices are also conceivable, based, for example, on induction currents. As a result of the heating, the columns 2 are brought to a higher temperature than the surroundings. Therefore, each column radiates energy depending on the temperature thereof—in the first order—in accordance with Planck's law. This has the consequence that within the isotropic region of the photonic crystal 1, that is, outside the resonator 4, a homogeneous distribution of electric field strength (100%, for example, 1 V/m) exists which decreases outside the photonic crystal 1, depending on shape and distance. In the resonator 4, a very strong field intensification is formed and modes arise, according to the geometry.

Figure 4:
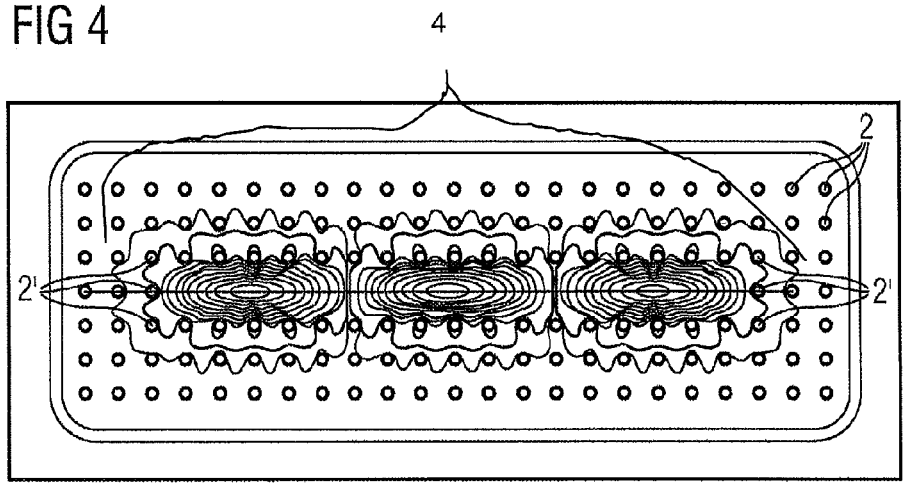
FIG. 4 is a schematic plan view of a "radiating" photonic crystal.
Figure 5:
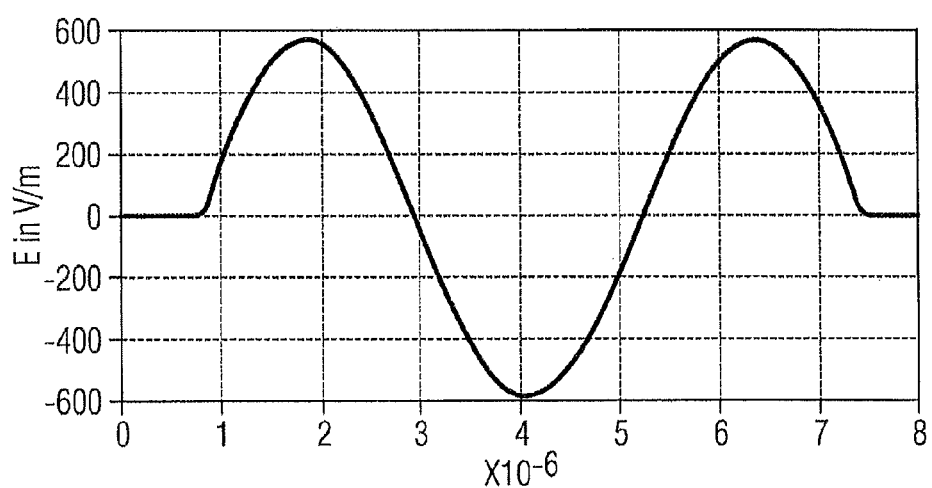
FIG. 5 is a graph of a field strength distribution in the "radiating" photonic crystal according to FIG. 4.

FIG. 4 shows the "radiating" photonic crystal 1 achievable by heating the columns 2. FIG. 5 shows, by way of example, an associated distribution of the electric field strength E along the resonator 4. The field strength is substantially greater than in the homogeneous photonic crystal and essentially depends on the length of the resonator 4, that is, in the example shown, on the number of columns missing in a row. Even where single columns (4 to 10) are missing, an electric field strength is produced in the resonator 4 which is several hundred times to several thousand times greater than the field strength in the region outside the resonator 4.

Figure 6:
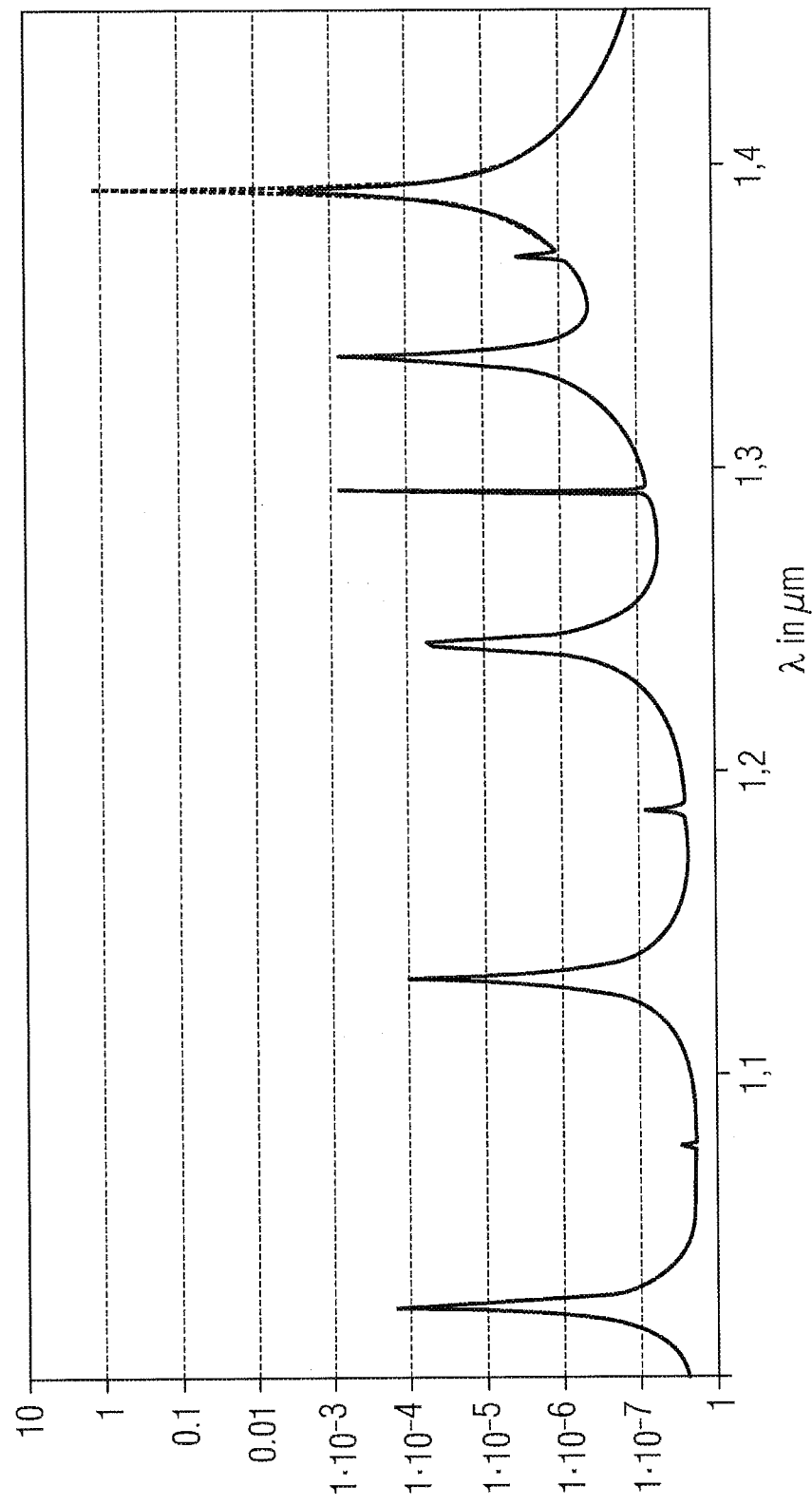
FIG. 6 is a graph representing a section of an intermediate product during the manufacturing of a three-dimensional photonic crystal following the creation of pores with periodically changing diameter in a substrate.

The electromagnetic radiation of the wavelength in resonance according to the geometry is multiplied in the resonator 4. Since other wavelengths are suppressed in the photonic crystal 1, the resonator 4 oscillates only in a very narrow wavelength region. FIG. 6 shows an exemplary relative intensity distribution of the electric field strength (Ez component) in the resonator 4 as a function of the wavelength 1. It is clearly shown that the main maximum (resonance peak), in this case at approximately 1.38 µm, has a significantly greater amplitude than the secondary maxima. This shows that the resonator 4 oscillates at essentially only one frequency, specifically the resonant frequency.

The resonator 4 is damped only by the absorption of radiation at each column forming the edge of the resonator 4. However, this energy is not actually lost, but serves indirectly for heating the columns.

For detection of the radiation in the resonator 4 or the change thereof as a result of external influences, different methods for introducing detector elements into the resonator are suitable. It is important herein that the damping of the resonator 4 is not too great when the detector elements are introduced, so that the internal amplification is not destroyed. It is desirable to use one or more columns as receivers, since the geometric resonator structure is disrupted to only an insignificant extent thereby.

Figure 7:
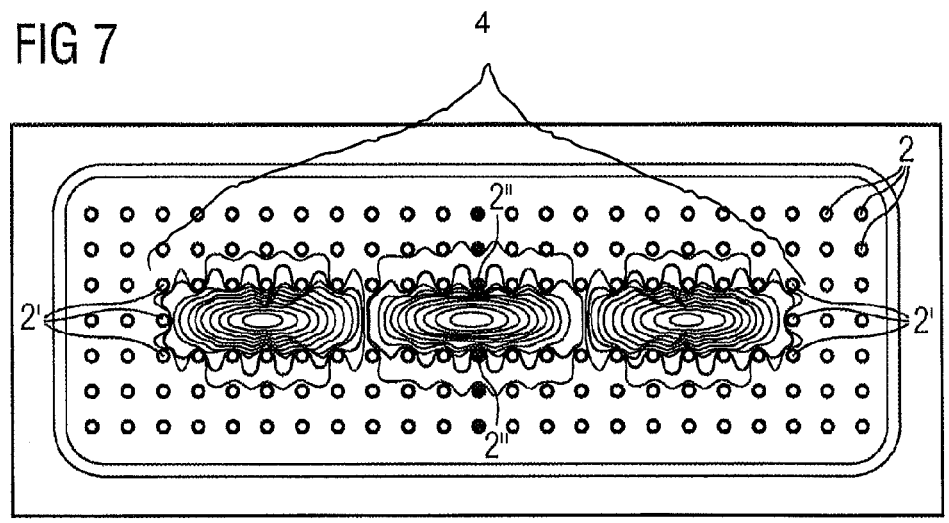
FIG. 7 is a schematic plan view of an intermediate product during the manufacturing of a three-dimensional photonic crystal following filling of the pores.
Figure 8:
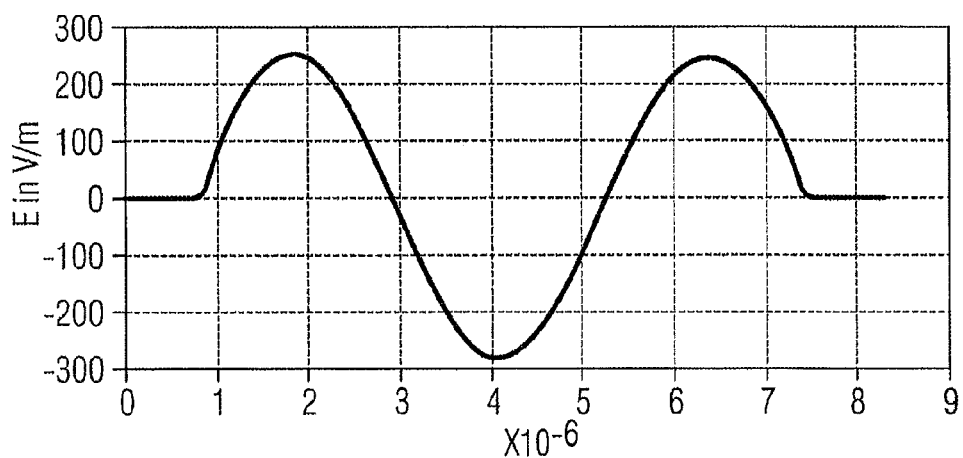
FIG. 8 is a graph representing a section of the three-dimensional photonic crystal following removal of the substrate material.

If, in place of a heated and therefore radiating column, a neutral, that is, unheated column 2" is used as a detector for the electric field strength in the resonator 4, the resonator 4 experiences damping depending on the length thereof. FIG. 7 shows the field strength distribution of a resonator 4 damped in this manner. FIG. 8 shows an exemplary associated field strength distribution along the resonator 4. It is apparent that, despite the damping, multiplication of the electric field strength by more than a factor of 100 remains.

If the power coupled into the neutral columns 2" acting as the detector element is determined with the spectral density of the field strength, a similar dependency on wavelength for the power transferred to the detector element as for the intensity distribution of the electric field strength results. Therefore, a very strong peak also results for the power transferred to the detector element in the resonance case.

If the geometry of the resonator is left unchanged and if individual columns 2" of the photonic crystal 1 are used as a detector element, the energy density present in the resonator 4 can thus be represented by the power transfer to the columns 2". In order to ensure the best possible power transfer, it is advantageous that the columns 2" serving as the detector element are arranged in the edge region of the resonator.

In order to determine the energy deposited in the resonator 4 as an electrical signal, for example two neutral columns 2" can be connected at the open end to a measuring loop with the aid of a conductor connection 8 (see FIGS. 1 and 2). If the temperature dependence of the inner material properties of the unheated columns 2" is used in the measuring loop, then conclusions can be drawn regarding the energy transmission. Since the neutral detector elements are not actively heated thermally, with the aid of the energy transmission from the resonator 4 to the neutral columns 2", conclusions can be drawn regarding the concentration of the gas components to be detected. The basic rule applies here that a high temperature indicates that only a little radiation has been absorbed in the resonator 4, that is, the gas component to be detected is present only in a low concentration and vice versa.

In order to determine the temperature influence, a variety of measuring principles are usable. For example, the temperature dependence of the specific resistance of the closed measuring loop can be used for a resistance measurement. If the neutral columns 2" forming the measuring loop are made of different materials, by way of alternative, a thermoelectric force or a thermoelectric voltage which forms in the presence of temperature differences between the open and closed ends of the measuring loop can be measured. The evaluation can be carried out with the aid of an evaluating unit 9, for example, in the form of an application-specific integrated circuit (ASIC) which is connected via electrical contacts 10 to the measuring loop. The ASIC can naturally also be used for controlling the heating device 5.

In order to achieve that the neutral columns 2" serving as the detector element remain unheated, thermal breaks 11 are provided in the thermal heating unit shown in FIG. 3 in which the material of the substrate 3 has been removed. How the neutral columns 2" are not actively heated is immaterial to the usability of the device.

If a resonator 4 is made to oscillate at a wavelength at which gas absorption by the gas components to be detected takes place in the device, the existence of specific gases can be selectively detected and, following suitable calibration, also the concentration thereof.

It is therein advantageous to provide columns 2 of the photonic crystal made of solid base material in the form of metal or metal alloy because the materials have a high refractive power and thus optimally support the effect of guiding the electromagnetic wave in the resonator 4. The intermediate spaces between the columns 2 permit the passage of the gas under investigation, so that the resonator 4 is exposed to the gas to be analyzed over a relatively large volume. In this manner, it is achieved that the damping of the resonator 4 is very sensitive to the gas absorption at the specific resonance wavelength. Since the resonance wavelength has a very sharp peak, a high degree of selectivity and therefore a high signal quality is assured.

The detection of the gas components to be detected is carried out very simply. Once the device has been exposed to the gas to be analyzed and at least a portion of the columns 2 of the photonic crystal 1 have been heated, the energy in the resonator 4 is extracted via the detector element. The principle that applies herein is that the higher the concentration of the gas component to be detected, the more strongly the radiation is absorbed and the lower is the field strength in the resonator 4 and thus the lower is the energy transferred to the detector elements. The existence of a gas component and/or the concentration thereof can thus be detected depending on the energy extracted.

The device has been described on the basis of a two-dimensional photonic crystal, although it can also be realized using a three-dimensional photonic crystal with columns which have a diameter which changes, in particular periodically, in the longitudinal direction.

By changing the ratio of diameter to spacing of the columns 2 of the photonic crystal, the resonance wavelength or resonant frequency can be tuned in a defined manner. In this way, the device can be matched to the individual gas components to be detected. However, this also offers the possibility of placing a plurality of such resonators with different resonant frequencies on a common substrate in a field adjoining one another and thus to cover any desired partial region of the overall spectrum.

Figure 9:
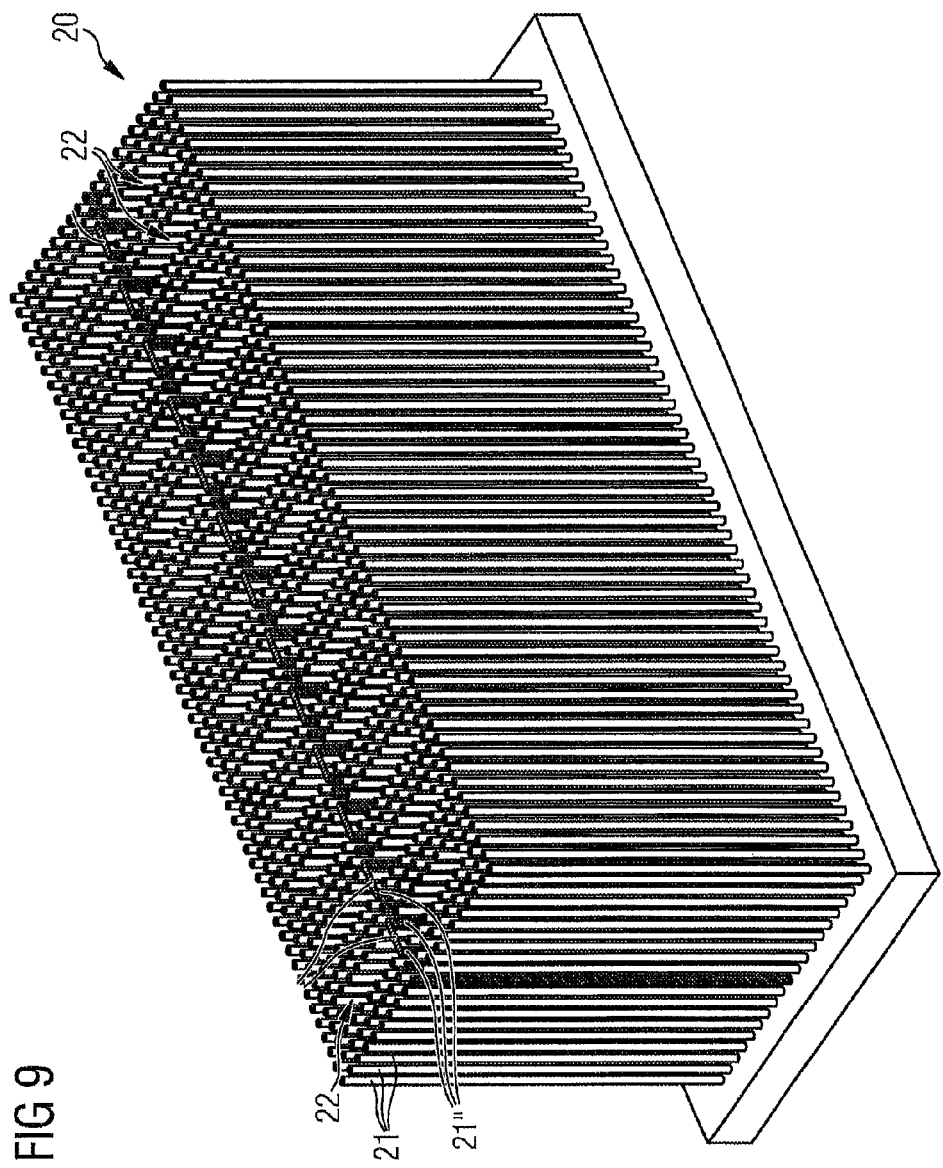
FIG. 9 is a schematic perspective representation of the three-dimensional photonic crystal according to FIG. 8.

FIG. 9 shows schematically a system for the selective detection of a plurality of gas components or concentrations of a plurality of gas components in a gas to be analyzed. Similarly to the device described above, the system includes a photonic crystal 20 which has a periodically arranged structure of free-standing columns 21, the base material of which is at least one metal or metal alloy, intermediate spaces between the columns permitting the passage of the gas to be analyzed. By pre-defined imperfections in the form of missing columns, a plurality of parallel resonators 22 are formed. The resonant frequencies of the individual resonators 22 are each in a frequency range which is absorbed the respective gas components to be analyzed. Also associated with each resonator 22 is a detector element in the form of two neutral, unheated columns 22" each of which is connected via a conductor connections 23 to measuring loops. The detector elements, for each of the resonators 22, can extract the energy present in the resonator 22 in the heated state, under the effect of the gas to be analyzed. Similarly to the device described above, again a heating device (not shown in FIG. 8) is naturally provided for heating at least a portion of the columns. Ultimately, therefore, a plurality of the devices are merely arranged parallel to one another on a common substrate 24.

By a suitable geometric configuration of a resonator, the device also enables the formation of a reference channel which may oscillate at a frequency having no or only slight gas absorption, so that transverse effects can be compensated for.

A description has been provided with particular reference to preferred embodiments thereof and examples, but it will be understood that variations and modifications can be effected within the spirit and scope of the claims which may include the phrase "at least one of A, B and C" as an alternative expression that means one or more of A, B and C may be used, contrary to the holding in *Superguide v. DIRECTV,* 358 F3d 870, 69 USPQ2d 1865 (Fed. Cir. 2004).

The invention claimed is:

1. A device for selectively detecting a gas component or a concentration of a gas component in a gas to be analyzed, comprising:
    a photonic crystal having a periodically arranged structure of free-standing columns formed from a base material of at least a metal or a metal alloy, with intermediate spaces between the free-standing columns that allow the gas to be analyzed to pass through, said photonic crystal having first predefined imperfections that provide at least one resonator with a resonant frequency in a frequency range absorbed by the gas component to be detected;
    a heating device heating at least a portion of the free-standing columns; and
    at least one detector element extracting energy present in the at least one resonator in a heated state when the gas to be analyzed is present.

2. The device as claimed in claim 1, wherein the free-standing columns have a diameter which changes, in particular periodically, in a longitudinal direction.

3. The device as claimed in claim 2, wherein the free-standing columns have a first ratio of length to diameter of greater than 100.

4. The device as claimed in claim 3, wherein a minimum column diameter is 0.3 µm.

5. The device as claimed in claim 4, wherein the diameter of the free-standing columns changes periodically in a second ratio of greater than 1:3.

6. The device as claimed in claim 5, wherein the free-standing columns are formed of at least one further material, the base material and the further material having a pre-defined structure, the further material including at least one material selected from the group consisting of metals, metal alloys, plastics, thermal oxides, other oxides and nitrides.

7. The device as claimed in claim 6, wherein the at least one detector element is formed by at least one unheated column of said photonic crystal.

8. The device as claimed in claim 7, wherein the at least one unheated column serving as the detector element is arranged in an edge region of the resonator.

9. The device as claimed in claim 8, wherein the at least one detector element is provided by at least two unheated columns of said photonic crystal.

10. The device according to claim 9, wherein the at least one detector element further comprises a measuring loop electrically connected to the at least two unheated columns.

11. The device as claimed in claim 10, wherein said photonic crystal further comprises second predefined imperfections forming at least one reference resonator having a reference frequency in a reference frequency range which is not absorbed by the gas component to be detected.

12. The device as claimed in claim 11, wherein the resonant frequency of the at least one resonator is determined by a third ratio of the diameter of the free-standing columns to a distance between the free-standing columns.

13. A method for selectively detecting gas components or a concentration of a gas component in a gas to be analyzed using a device including a photonic crystal having a periodically arranged structure of free-standing columns formed from a base material of at least a metal or a metal alloy, with intermediate spaces between the free-standing columns that allow the gas to be analyzed to pass through, the photonic crystal having predefined imperfections that provide at least one resonator with a resonant frequency in a frequency range absorbed by the gas component to be detected; a heating device and at least one detector element. said method comprising:
    exposing the device to the gas being analyzed;
    heating at least a portion of the free-standing columns of the photonic crystal;
    extracting, by the detector element, energy present in the at least one resonator in a heated state when the gas to be analyzed is present; and
    detecting existence and/or concentration of the gas component depending on the energy extracted.

14. A system for selectively detecting at least two gas components or concentrations of at least two gas components in a gas to be analyzed, comprising:
    a photonic crystal having a periodically arranged structure of free-standing columns formed from a base material of at least a metal or a metal alloy, with intermediate spaces between the free-standing columns that allow the gas to be analyzed to pass through, said photonic crystal having first predefined imperfections that provide at least two resonators, each having a resonant frequency in a frequency range absorbed by a different gas component to be detected;
    a heating device heating at least a portion of the free-standing columns; and
    at least one detector element for each resonator, extracting energy present in a corresponding resonator in a heated state when the gas to be analyzed is present.

* * * * *